United States Patent [19]

Jallageas et al.

[11] 4,366,250

[45] Dec. 28, 1982

[54] PREPARATION PROCESS OF OPTICALLY ACTIVE α-AMINATED ACIDS BY BIOLOGICAL HYDROLYSIS OF NITRILES

[75] Inventors: Jean C. Jallageas, Montpellier; Alain Arnaud, Clermont L'Herault; Pierre Galzy, Montpellier, all of France

[73] Assignee: Anvar, Paris, France

[21] Appl. No.: 209,402

[22] PCT Filed: Jan. 24, 1980

[86] PCT No.: PCT/FR80/00008

§ 371 Date: Sep. 24, 1980

§ 102(e) Date: Sep. 19, 1980

[87] PCT Pub. No.: WO80/01571

PCT Pub. Date: Aug. 7, 1980

[51] Int. Cl.³ ............................................. C07B 19/02
[52] U.S. Cl. ........................................................ 435/280
[58] Field of Search .................................. 435/280, 42

[56] References Cited

U.S. PATENT DOCUMENTS 2,511,867  6/1950  Neuberg et al. ................... 435/280
3,635,795  1/1972  Demain et al. .................... 435/280
3,971,700  7/1976  Boester ............................... 435/280
4,080,259  3/1978  Boester et al. ................. 435/280 X

FOREIGN PATENT DOCUMENTS 2245585  4/1975  France .
2294999  7/1976  France .
2337761  8/1977  France .

OTHER PUBLICATIONS

Chemical Abstracts, vol. 89, No. 19, 161521y; 19786.

Primary Examiner—Robert J. Warden
Attorney, Agent, or Firm—Maky, Renner, Otto & Boisselle

[57] ABSTRACT

This process for preparing L α-amino-acid is characterized in that the corresponding racemic α-amino-acid is hydrolysed in liquid phase in a free form or in the form of a salt, by an agent containing an L-stereospecific amidase and in that the L α-amino-acid obtained is separated from the D α-amino-amid unhydrolysed. This process is appropriate for the preparation of optically active natural amino-acids.

7 Claims, No Drawings

PREPARATION PROCESS OF OPTICALLY ACTIVE α-AMINATED ACIDS BY BIOLOGICAL HYDROLYSIS OF NITRILES

The present invention concerns itself with a preparation process of optically active α-aminated acids by biological hydrolysis of corresponding α-amino amides or of corresponding α-amino nitriles.

Formerly the optically active α-aminated acids were prepared from racemic amino acids by resolution of stereoisomeres by the already known method, in particular by the formation of salts with other optically active compounds or by the resorting to resins, which offer certain stereospecific characteristics.

In addition to the fact, that these technical procedures are very delicate to be put into operation, they naturally impose an additional step at the time of the synthesis of amino acids from other products like the corresponding amino amides or the corresponding amino nitriles, which, generally, are the normal precursors of these amino acids.

Now, the present invention proposes a process, which will permit the direct preparation of the amino acid in optically active form, either from amino amides or from amino nitriles.

For this purpose, the present invention concerns itself with a process of preparation of Lα-amino acids, characterized by the fact, that the corresponding racemic α-amino amide is hydrolized in a liquid medium by an agent, which contains a L stereospecific amidase, and further, that the Lα-amino acid, obtained from the non-hydrolized Dα-amino amide, is then separated.

In a preferable method of operation pursuant to this invention the racemic Lα-amino amide is prepared in situ from the corresponding Lα-amino nitrile by action of an agent, which contains a general nitrilase.

In the following statements the terms "amino amide" or "amino nitrile" or "amino acid" comprise also the compounds in free form or in the form of salt, particularly of hydrochloride.

The agents, which are used in the framework of this invention, are preferably bacteria or non-cellular preparations of bacterial origin, which do not possess general amidase.

In the event, that the α-amino acid is prepared from the corresponding α-amino nitrile, it is especially interesting to note, that the bacterium or the a(non)-cellular preparation of bacterial origin possess both the L stereospecific amidase and the general nitrilase in such a manner, that only one source (mother liquid) or a(non)-cellular preparation of bacterial origin has to be used.

Of course, it is possible, by proceeding with nitrile, to effect the reaction in two steps, using two agents, which separately possess, the one the L stereospecific amidase, the other the general nitrilase.

The bacteria or the a(non)-cellular preparations of bacterial origin, come preferably from a mutant of a strain, which itself possesses a general amidase, which mutant is able to grow in a nutrient medium, containing monofluor acetamide through the loss of the general amidase.

Actually, it has been found, that in the event that strains which possess a general amidase, are made to grow in a nutrient medium containing monofluor-acetamide, they transform the monofluor-acetamide into monofluor acetic acid according to the reaction:

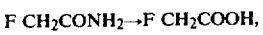
$$F\ CH_2CONH_2 \rightarrow F\ CH_2COOH,$$

which is toxic for these bacteria and which has evidently the effect to make spontaneous defective mutants appear, which means, they no longer possess the general amidase, but only the L stereospecific amidase.

The mutants thus obtained are spontaneous mutants, but, of course, it is possible to utilize the known mutagene agents, like ultraviolet radiation, X or γ or the chemical compounds like ethylmethane sulfonate, nitrous acid, alkylating agents, nitroso-guanidine, or acryflavine, for example, in order to increase the frequency of appearance of strains, which possess the L stereospecific amide base.

Among the strains, which possess a general amidase, one has to cite particularly the genus Bacillus, Bacteridium as defined by Prevot, Micrococcus and Brevibacterium as defined by Bergey. As regards the more preferred, these bacteria are chosen among the strains of the collection of the Professorship for Genetics and Microbiology of the National Superior Agronomic School of Montpellier (R 332, R 340, R 341, A 111, B 222, A 112, A 13, A 141, A 142, B 211, B 212, B 221, C 211, R 21, R 22, R 311, R 312, R 331 or among those, which are deposited in the Centraalbureau voor Schimmelcultures under the numbers: 717-73, 494-74, 495-74, 496-74, 497-74, 498-74, 499-74.

These strains possess a general amidase, which present the following mutual characteristics:

Gram Positive, negative alcohol-acid resistance.
Strict Aerobiosis; positive catalase.
Utilization of glucose, sucrose, maltose and lactose by oxydation without production of gas and without acidification.
None of the strains forms alcohol. The starch is not hydrolized, but there is growth on potato.
Search test for tyrosine on potato: negative.
Need of vitamins.
Absence of hydrolysis of gelatine.
Growth on ammonia and on nitrates as only source of nitrogen.
No discharge of hydrogen sulfide.
Absence of growth in hypersalted bouillon.

CHART I

| | | MORPHOLOGIC CHARACTERISTICS | | |
|---|---|---|---|---|
| Source | Spore | Mobility | Cellular Morphology | Morphology of settlements |
| R 332 | + | weak | Rod Bacteria $(1.8-3.6)\mu \times 0.9\mu$ | Circular, smooth, convex, rose, at the whole edge |
| R 340 | + | − | Rod Bacteria $2.7\mu \times 0.9\mu$ | Circular, small, white, at diffused edge |
| R 341 | + | − | Rod Bacteria $2.7\mu \times 0.9\mu$ | Dense, very granulous, white, flat |
| A 111 | − | − | Shells | Circular, small, folded, convex, rose at lobed edge |
| B 222 | − | + | Rod Bacteria | Circular, small, yellow-orange |

CHART I-continued

MORPHOLOGIC CHARACTERISTICS

| Source | Spore | Mobility | Cellular Morphology | Morphology of settlements color |
|---|---|---|---|---|
| A 112 | — | weak | $(3.6-4.5)\mu \times 0.9\mu$ Rod Bacteria | Small, opaque, set off, at lobed edge, rose orange |
| A 13 | — | weak | $(1.8-3.6)\mu \times 0.9\mu$ Rod Bacteria | Circular, smooth, opaque, orange-rose, at the whole edge |
| A 141 | — | — | $2.2\mu \times 0.9\mu$ Rod Bacteria | Small, almost flat, opaque, Granulous, orange-rose, at lobed edge |
| A 142 | — | — | $(1.8-3.6)\mu \times 0.9\mu$ Rod Bacteria | Circular, smooth, opaque, orange, at whole edge |
| B 211 | — | — | $(3.6-4.5)\mu \times 0.9\mu$ Rod Bacteria | Circular, bulged, small, smooth, rose, at the whole edge |
| B 212 | — | — | $1.8\mu \times 0.9\mu$ Rod Bacteria | Circular, bulged, smooth, rose, at the whole edge |
| B 221 | — | weak | $3.6\mu \times 0.9\mu$ Rod Bacteria | Circular, very lobed, set off, of yellow-orange color |
| C 211 | — | weak | $(3.6-4)\mu \times 0.9\mu$ Rod Bacteria | Circular, smooth, shiny, rose, at the whole edge |
| R 21 | — | — | $(3.6-8.1)\mu \times 0.9\mu$ Rod Bacteria | Circular, flat, rose granulous, at the edge slightly lobed |
| R 22 | — | weak | $5.4\mu \times 0.9\mu$ Rod Bacteria | Circular, smooth, orange, set off, at the whole edge |
| R 311 | — | weak | $2.7\mu \times 0.9\mu$ Rod Bacteria | Circular, yellow, set off, at the whole edge |
| R 312 | — | — | $(1.8-3.6)\mu \times 0.9\mu$ Rod Bacteria | Circular, convex, yellow at the whole edge |
| R 331 | — | — | $(4.5-9)\mu \times 0.9\mu$ Rod Bacteria $4.5\mu \times 0.9\mu$ | Circular, rose, diffused and opaque level |

CHART II

PRINCIPAL PHYSIOLOGICAL FEATURES

| Source | Oxide Test | Indole | Acid Citric Utilization | Hydrolysis of Egg White | pH Optimum | Acetyl Methyl carbinol production |
|---|---|---|---|---|---|---|
| R 332 | — | — | — | — | 6.5 | strong |
| R 340 | — | + | + | — | 6.5 | — |
| R 341 | — | + | — | — | 6.0 | — |
| A 111 | — | + | + | light | 6.5 | weak |
| B 222 | + | — | + | — | 6.0 | — |
| A 112 | — | + | + | — | 6.5 | — |
| A 13 | — | + | — | — | 6.0 | weak |
| A 141 | — | — | + | — | 6.5 | weak |
| A 142 | — | + | + | — | 6.0 | weak |
| B 211 | — | + | + | — | 6.5 | strong |
| B 212 | — | — | + | + | 6.0 | — |
| B 221 | — | + | + | — | 6.5 | — |
| C 211 | — | + | — | — | 6.0 | — |
| R 21 | — | + | + | — | 7.5 | — |
| R 22 | — | + | + | — | 6.0 | — |
| R 311 | — | + | + | — | 6.0 | weak |
| R 312 | — | — | + | light | 6.0 | — |
| R 331 | — | + | — | + | 6.0 | — |

All the strains produce ammonia at the end of the culture on nitrate; in addition, they produce nitrite except the strains B 221, B 211, B 212 and C 211. Strain B 222 gives a gaseous discharge from the nitrates.

Strain R 332 belongs to the type Bacillus, but offers a weak proteolytic activity. Strain R 340 and R 341 are close to the type Bactiridium as defined by Prevot. The other strains are a(non)-sporulated. Strain A 111 is a Micrococcus. All the others are close to the type Brevibacterium as defined by Bergey. It is to be noted, that the strain B 222 is very close to the *Brevibacterium imperial*.

Among the sources, which can be utilized and which possess a L stereospecific amidase and a general nitrilase, one must cite especially the strain A4, deposited under number LMD 79.2 at the Centraalbureau voor Schimmelcultures on March 6, 1979.

The process pursuant to this invention permits, therefore, to obtain both the Lα-amino acid and the non-hydrolized Dα-amino amide. The latter amide can be racemized, then retreated, pursuant to the process of this invention in order to prepare a new quantity of Lα-amino acid. The racemization can be conducted by the known method, in particular by heating in the presence of ketone or acid.

On the other hand, as has been noticed, that the different above mentioned strains possess a general amide base, but do not possess racemase, if one treats the Dα-amino amide obtained by these strains, one obtains directly the corresponding Dα-amino acid.

The invention covers also the use of Dα-amino amide obtained by hydrolysis for preparation of corresponding Dα-amino acid in presence of an agent, containing a general amidase like the above described strains.

The process, pursuant to the present invention, permits, therefore, to prepare in pure condition the two stereo-isomeres, well isolated.

Of course, although it might be preferable to utilize the bacteria, as the process, according to this invention, does not necessitate the growth of bacteria, it is equally possible to utilize the a(non)-cellular preparations originating from these bacteria, which can present themselves, for example, in the form of fixed enzymes or in the form of branched or fixed cells on a support or absorbed by it, which can, in certain cases, facilitate their manipulation.

The process pursuant to this invention permits, therefore, to obtain the optically active α-amino acids as, for example, the α-alanine, methionine, phenylalanine, leucine, valine.

It is equally possible, of course, to synthetize the α-amino acids in their optically pure form D.

Finally, it is possible to obtain α-amino acids optically active, which do not figure among the usual components of proteins.

Although the parameters in performing the process pursuant to this invention are not critical, it is satisfactory to operate at the temperature and pressure of the environment.

The process is preferably conducted in an aqueous medium. Although in certain cases the slight solubility in water of nitrile poses a problem, it does not to any extent hinder the nitrilasic or the L-amidasic activity of the bacteria, which are used in the process pursuant to this invention.

One advantage of the process pursuant to this invention, is the possibility of recycling the bacteria, which are still active at the end of the process.

Lastly, the pH of the medium is preferably held between 6 and 9.

The following examples are given for the purpose of illustrating the operation of the process according to this invention, without, of course, limiting in any manner to said examples.

EXAMPLE 1

Preparation of mutant A4

A mass display of a culture of strain CBS 717.73 on "Yeast natural broth" (YNB)-ammonium acetate 0.5%-fluoro-acetamide 1% gelose (pH 6.5) is effected. In a period of 8 to 10 days, resistant colonies appear; They are sampled on a YNB-ammonium acetate 0.5% medium without fluoroacetamide (pH 6.5). Their resistance to fluoro-acetamide is then tested in a liquid medium comparative to the wild strain. The mutant strain is then tested in a liquid medium, comparative to the wild strain. The mutant strain is then spread on YNB-ammonium acetate 0.5% (pH 6.5) to verify the homogeny and then a "replica plating" on YNB-acetamide 0.5% (pH 6.5) and YNB-ammonium acetate 0.5%-fluoro-acetamide 1% (pH 6.5) is effected. Several defective mutants have in this way been screened from source R 312 (CBS 717.73).

They are stable in vegetative multiplication. Only one mutant has been utilized in these applications: the strain A4 (Collection of the Professorship of Genetics and Microbiology).

EXAMPLE 2

Preparation of L-Methionine from α-amino-X-methylthiobutyronenitrile DL hydrochloride A solution of 6% of α-amino-γ-methylthiobutyronitrile hydrochloride (pH held between 6.5 and 8.5) is treated with bacteria of strain A4 at a concentration of about 30 g of dry matter per liter. The transformation is quantitative in L-methionine (50%) and in corresponding D-amide (50%) in 2 to 3 hours. The products are separated by the known technical procedure. The amide D is racemized and can be recycled.

EXAMPLE 3

Preparation of D-methionine from α-amino-γ-methylthiobutyronenitrile DL hydrochloride The treatment starts under the same conditions as above described. After separation, the α-amino-γ-methylthiobutyramide D is treated by bacteria of the strain R 312 (CBS 717.73) under the same conditions. In this manner, D-methionine is obtained. The hydrolysis of α-amino-γ-methylthiobutyronenitrile permits in this manner to obtain, well separated, L-methionine and D-methionine.

EXAMPLE 4

Preparation of L-methionine from α-amino-γ-methylthiobutyramide DL hydrochloride The treatment of a solution of 6% of α-amino-γ-methylthiobutyramide DL hydrochloride in water (pH 6.5 to 8.5) is effected by a suspension of cells of the strain A4 at 20 to 40 g per liter of dry matter. One obtains quantitatively L-Methionine (50%) and D-methionamide (50%). This amide D can be either hydrolized in D-methionine by action of source R 312 (CBS 717.73), or racemized and recycled as regards the preparation of L-methionine.

EXAMPLE 5

Preparation of L-phenylalanine from hydrochloride of 2-amino-3-phenyl propionitrile DL A solution of 5% of hydrochloride of 2-amino-3-phenyl propionitrile (pH included between 6.5 and 8.5) is treated by the bacteria of strain A4 at a concentration of 20 to 40 g of dry matter per liter. The transformation is quantitative into L-phenylalanine (50%) and into corresponding D-amide (50%) in 2 to 3 hours. The products are separated by the known technical procedures. The amide D is racemized and can be recycled.

EXAMPLE 6

Preparation of D-phenylalanine from 2-amino-3-phenyl propionitrile DL hydrochloride The treatment starts under the above-described conditions. After separation, 2-amino-3-phenyl propionamide D is treated by the bacteria of the strain R 312 (CBS 717.73) under the same conditions. Thus D-phenylalanine is obtained. The hydrolysis of 2-amino-3-phenyl propionitrile permits thus to obtain, well separated, the L-phenylalanine and the D-phenylalanine.

EXAMPLE 7

Preparation of L-phenylalanine from 2-amino-3-phenyl propionamide DL hydrochloride The treatment of a solution at 5% of 2-amino-3-phenyl propionamide hydrochloride in water (pH included between 6.5 and 8.5) is effected by a suspension of cells of strain A4 at 20 to 40 g of dry matter per liter. One obtains quantitatively L-phenylalanine (50%) and the corresponding D-amide (50%). This D amide can either be hydrolized in D-phenylalanine by action of strain R 312 (CBS 717.73) or racemized and recycled in regard to preparation of L-phenyl-alanine.

EXAMPLE 8

Preparation of L-α-alanine from hydrochloride of α-aminopropionitrile DL

A solution of 6% of hydrochloride of α-amino-propionitrile in water (pH included between 6.5 to 8.5) is treated by bacteria of the strain $A_4$ at a concentration of 20 to 40 g of dry matter per liter. The transformation is quantitative into L-α-alanine (50%) and into D-α-aminopropionamide (50%) in 2 to 3 hours. The products are separated by the known technical procedures. The amide D is racemized and can be recycled.

EXAMPLE 9

Preparation of D-α-alanine from hydrochloride of α-aminopropionitrile DL

The treatment starts under the same conditions as stated above. After separation the α-amino-propionamide D is treated by the bacteria of strain R 312 (CBS 717.73) under the same conditions. Thus D-α-alanine is obtained. The hydrolysis of the α-aminopropionitrile permits thus to obtain L-α-alanine and D-α-alanine, well separated.

EXAMPLE 10

Preparation of L-α-alanine from hydrochloride of α-aminopropionamide DL

The treatment of one solution at 6% of hydrochloride of α-aminopropionamide in water (pH included between 6.5 to 8.5) can be effected by a suspension of cells of strain $A_4$ at 20 to 40 g of dry matter per liter. Quantitatively L-α-alanine (50%) and D-α-aminopropionamide (50%) is obtained. This amide D can either be hydrolized in D-α-alanine by action of strain R 312 (CBS 717.73) or racemized and recycled with a view to the preparation of L-α-alanine.

We claim:

1. A process for the preparation of L-alpha-amino acid from the corresponding racemic alpha-aminonitrile in free form or as salt comprising hydrolizing in a single step in liquid medium racemic alpha-aminonitrile in free form or as a salt with a bacteria having a general nitrilase and a L-stereospecific amidase and isolating the L-alpha amino acid from the D-alpha-amino amide.

2. Process pursuant to claim 1 wherein said bacteria is derived from a strain or mutant of a strain which possesses a L-sterospecific amidase, said strain being strain $A_4$ deposited under No. LMD 79.2, which is free from a general amidase.

3. Process pursuant to claim 2, characterized by the fact, that the hydrolysis is conducted at a pH, between 6 and 9 inclusive.

4. Process pursuant to claim 3 characterized by the fact, that said liquid medium is an aqueous medium.

5. A process pursuant to claim 1 wherein said bacteria is derived from a strain or mutant of a strain which possesses a general amidase, the process including the steps of growing said bacteria on a medium containing monofluoro-acetamide and selecting mutants with a general nitrilase and a L-stereospecific amidase.

6. Process pursuant to claim 5, characterized by the fact, that the strain, which possess a general amidase, are chosen from the types Bacillus, Bacteridium, Micrococcus and Brevibacterium.

7. Process pursuant to claim 5, characterized by the fact, that the strains, which possess a general amidase are chosen among the strain No. R 332, R 340, R 341, A 111, B 222, A 112, A 13, A 141, A 142, B 211, B 212, B 221, C 211, R 21, R 22, R 311, R 312, R 331, deposited at the Professorship for Genetics of the National Superior Agronomic School of Montpellier.

* * * * *